United States Patent [19]

Schirmann et al.

[11] 4,128,494

[45] Dec. 5, 1978

[54] ACTIVATORS FOR PERCOMPOUNDS

[75] Inventors: Jean-Pierre Schirmann, Oullins; Bernard Dubreux, Francheville le Bas; Michel Bakes, La Celle Saint Cloud; Serge-Yvon Delavarenne, Francheville le Haut; Marie-Christine Daude-Lagrave, Paris, all of France

[73] Assignee: Produits Chimiques Ugine Kuhlmann, Paris, France

[21] Appl. No.: 822,145

[22] Filed: Aug. 5, 1977

[51] Int. Cl.$^2$ .................... C11D 3/395; C11D 7/54; D06L 3/02

[52] U.S. Cl. .................... 252/186; 8/107; 252/95; 252/99; 252/103; 423/272; 424/62

[58] Field of Search ............ 252/186, 95, 99, 103; 8/107; 260/404.5 R, 610 A; 423/272; 424/62; 426/257, 258, 261

[56] References Cited

U.S. PATENT DOCUMENTS

| | | | |
|---|---|---|---|
| 2,927,840 | 3/1960 | Dithmar et al. | 252/186 |
| 3,969,257 | 7/1976 | Murray | 252/186 |
| 3,986,972 | 10/1976 | Loffelman et al. | 252/186 |
| 4,003,700 | 1/1977 | Gray et al. | 252/186 |

*Primary Examiner*—Benjamin R. Padgett
*Assistant Examiner*—Irwin Gluck

*Attorney, Agent, or Firm*—Brooks, Haidt, Haffner & Delahunty

[57] ABSTRACT

Novel percompound activators having the formula

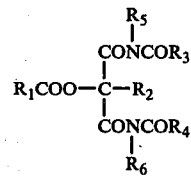

wherein $R_1$, $R_2$, $R_3$, $R_4$, $R_5$, and $R_6$ are the same or different and are hydrogen or certain substituted or unsubstituted straight or branched chain alkyl radicals, cycloalkyl radicals, or hydrocarbon radicals containing at least one aromatic ring, or $R_5$ and/or $R_6$ are $COR_7$, where $R_7$ is hydrogen or certain substituted or unsubstituted straight or branched chain alkyl radicals or hydrocarbon radicals containing at least one aromatic ring, the activators producing more rapid bleaching or oxidation at a given temperature or the same bleaching effect at a lower temperature and being useful for bleaching textile fibers, oils, fats, and waxes; hair and skin treatment; metal surface passivation; or purifying, sterilizing and disinfecting techniques.

7 Claims, No Drawings

ACTIVATORS FOR PERCOMPOUNDS

BACKGROUND OF THE INVENTION

The present invention relates to the use of α-acyloxy-N,N'-polyacylmalonamides as activators for mineral and organic percompounds, and more particularly, as activators for hydrogen peroxide, for its addition products with organic substances such as urea and dicyclohexylamine, and also of its mineral persalts such as perborates, percarbonates and perphosphates.

The action of aqueous solutions of percompounds as oxidizing and bleaching agents becomes effective only at temperatures above 70° C. and preferably between 80° and 100° C.

The prior art describes numerous products exhibiting the property of acting as percompound activators, that is, permitting the achievement of a more rapid oxidizing or bleaching action than that which is customarily observed, or alternatively developing such action under much gentler temperature conditions than those which it is necessary to use in their absence, all these percompounds being characterized by the fact that they have one or more perhydrolyzable functions.

In the bleaching field, a certain number of activator compounds have begun to be developed commercially. The literature on this subject mentions especially poly-N-acetylated heterocycles of the hydantoin, glycoluril, benzimidazole and diketopiperazine type. However, this development has not been pursued because these substances display the major disadvantage of being unstable with reference to ambient humidity and of hydrolyzing spontaneously, thus rapidly losing their activator property.

Moreover, these products require special precautions for storage, handling or the addition of other ingredients, such as those used for instance in the usual washing powder compositions. Various solutions have been proposed to overcome this disadvantage: coating, separate packing, or addition of desiccating products, but these have not given satisfaction, either because they present technical problems in practical usage or because they lead to a considerable increase in the cost of the active substance.

There therefore exists an industrial need for available percompound activators which are stable for long periods in the solid state under normal conditions of storage and packing.

THE INVENTION

The present invention provides as percompound activators α-acyloxy-N,N'-polyacylmalonamides of the formula:

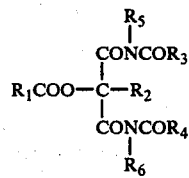

wherein $R_1$, $R_2$, $R_3$, $R_4$, $R_5$, and $R_6$ are the same or different, and are chosen from among hydrogen, the straight chain alkyl radicals with from one to eleven carbon atoms, the branched chain alkyl and cycloalkyl radicals with from three to twelve carbon atoms, hydrocarbon radicals with from six to twelve carbon atoms comprising at least one aromatic ring, or wherein $R_1$, $R_2$, $R_3$, $R_4$ are defined as hereinbefore, while $R_5$ and/or $R_6$ correspond to an acyl group, $COR_7$, wherein $R_7$ is hydrogen or a straight chain or branched alkyl radical with from one to twelve carbon atoms or a hydrocarbon radical with from six to twelve carbon atoms comprising at least one aromatic ring. These radicals are optionally substituted by one or more functional groups such as the hydroxy, chloro, bromo, fluoro, iodo, nitro, alkoxy, amino, ester, amide, ether groups, and the like.

Purely by way of illustration, examples of α-acyloxy-N,N'-polyacylmalonamides useful as percompound activators according to the present invention are α-acetoxy-α-methyl-N,N'-diacetylmalonamide, α-propionoxy-α-ethyl-N,N'-dipropionylmalonamide, α-acetoxy-α-methyl-N,N'-dipropionylmalonamide, and the like.

According to requirements, it is possible to operate with a deficit or an excess of activator, desirably with a molar ratio of activator to percompound between 0.1 and 10. A particularly preferred embodiment of the use of the activators according to the present invention is to add them to the percompound at the rate of approximately 0.5 mol of activator per mol of percompound to be activated.

The activators according to this invention can be used in all cases where a percompound is used to obtain an oxidizing or bleaching action. For example, they are very useful in the bleaching of textile fibers, oils, greases and waxes; hair and skin treatment in cosmetology; the passivation of metallic surfaces; and purification, disinfection and sterilization techniques.

The activators of the invention when added to the percompound or to a formula containing one or more percompounds, for example, a washing powder, make it possible to obtain a more rapid bleaching or oxidizing effect at a given temperature. They likewise make it possible to obtain the same bleaching effect when operating at a lower temperature.

For instance, in the presence of sodium perborate in a washing powder medium, the activators according to the invention make it possible to obtain, at temperatures of between 30° C. and 50° C., a bleaching action substantially equivalent to that obtained in their absence at high temperatures of the order of 80° C.

The following examples are given to illustrate embodiments of the invention as it is presently preferred to practice it. It will be understood that these examples are illustrative, and the invention is not to be considered as restricted thereto except as indicated in the appended claims.

EXAMPLES I TO III

Into a compartment of an AHIBA water bath heated to 40° C., there is introduced 250 ml of an aqueous solution containing 5 g per liter of a washing powder having the following composition:

| Constituent | Percent by weight |
| --- | --- |
| $Na_2SiO_3$ | 5.34 |
| $Na_2SO_4$ | 7.25 |
| $Na_2CO_3$ | 2.65 |
| $Na_2HPO_4$ | 0.96 |
| $Na_4P_2O_7$ | 3.99 |
| $Na_5P_3O_{10}$ | 30.41 |
| $NaPO_3$ | 11.92 |
| $H_2O$ | 18.9 |
| Surfactants | 14 |

| Constituent | Percent by weight |
|---|---|
| Optical brightener, various, to make | 100 | and 1.7 per liter of sodium perborate tetrahydrate.

Into the other compartment, the same solution is placed with the further addition of the activator to be tested, at the concentration of 1 g per liter.

Into each of the compartments there is placed a piece of "EMPA" cotton fabric impregnated with standardized wine stains, supplied by the Saint-Gall, Switzerland, laboratory. After 15 minutes of washing, the swatches are rinsed in a current of cold water, then dried at ambient temperature.

The bleaching power is defined by the difference between the whiteness indices (measured by means of a Carl Zeiss "ELREPHO" spectrophotometer and No. 6 filter) before and after washing, reduced to a percentage with a maximum whiteness of 100.

$$\text{Bleaching power (\%)} = \frac{\text{Difference in whiteness}}{100 - \text{Initial whiteness}} \times 100$$

| Ex. No. | Activator Name | Concentration, g/L | Bleaching Power (%) Without activator | With activator |
|---|---|---|---|---|
| I | α-Acetoxy-α-methyl-N,N'-diacetyl-malonamide | 1 | 40 | 61.5 |
| II | α-Propionoxy-α-ethyl-N,N'-dipropionyl-malonamide | 1 | 40 | 59.5 |
| III | α-Acetoxy-α-methyl-N,N'-dipropionyl-malonamide | 1 | 40 | 61.5 |

EXAMPLES IV TO VI

The tests are repeated under the operating conditions as hereinbefore, but with a washing temperature of 20° C instead of 40° C.

| Ex. No. | Activator Name | Concentration, g/L | Bleaching Power (%) Without activator | With activator |
|---|---|---|---|---|
| IV | α-Acetoxy-α-methyl-N,N'-diacetyl-malonamide | 1 | 31.5 | 45.3 |
| V | α-Propionoxy-α-ethyl-N,N'-dipropionyl-malonamide | 1 | 31.5 | 43.8 |
| VI | α-Acetoxy-α-methyl-N,N'-dipropionyl-malonamide | 1 | 31.5 | 44.8 |

What is claimed is:

1. An activated percompound composition comprising an organic or inorganic percompound and at least one α-acyloxy-N,N'-polyacylmalonamide activator having the formula

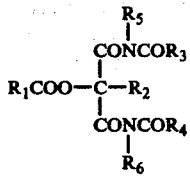

wherein $R_1$, $R_2$, $R_3$, $R_4$, $R_5$, and $R_6$ are the same or different and are hydrogen, straight-chain alkyl radicals having from one to eleven carbon atoms, branched chain alkyl or cycloalkyl radicals having from three to twelve carbon atoms, or hydrocarbon radicals with from six to twelve carbon atoms comprising at least one aromatic ring, or where one or both of $R_5$ and $R_6$ are $COR_7$ and $R_7$ is hydrogen, a straight chain or branched chain alkyl radical with from one to twelve carbon atoms or a hydrocarbon radical with from six to twelve carbon atoms comprising at least one aromatic ring, the activator being in an amount sufficient to increase the activity of the percompound.

2. A composition according to claim 1 wherein one or more of the activator radicals is substituted by a hydroxy, chloro, bromo, fluoro, iodo, nitro, alkoxy, amino, ester, amide or ether group.

3. A composition according to claim 1 wherein the molar quantity of activator is from about 0.1 to about ten times the molar quantity of percompound.

4. A composition according to claim 1 wherein the molar quantity of activator is about 0.5 times the molar quantity of percompound.

5. A detergent composition containing a percompound and an activator according to claim 1.

6. A process for activating percompounds which process comprises adding to the percompound a sufficient quantity of an activator, which activator has the formula

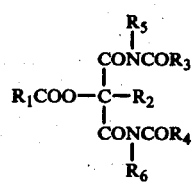

wherein $R_1$, $R_2$, $R_3$, $R_4$, $R_5$, and $R_6$ are the same or different and are hydrogen, straight-chain alkyl radicals having from one to eleven carbon atoms, branched chain alkyl or cycloalkyl radicals having from three to twelve carbon atoms, or hydrocarbon radicals with from six to twelve carbon atoms comprising at least one aromatic ring, or where one or both of $R_5$ and $R_6$ are $COR_7$ is hydrogen, a straight chain or branched chain alkyl radical with from one to twelve carbon atoms or a hydrocarbon radical with from six to twelve carbon atoms comprising at least one aromatic ring, to increase the activity of the percompound.

7. A process for bleaching which process comprises treating a substrate with a percompound in the presence of an activator, which activator has the formula

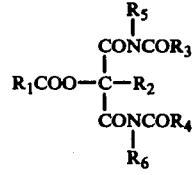

wherein $R_1$, $R_2$, $R_3$, $R_4$, $R_5$, and $R_6$ are the same or different and are hydrogen, straight-chain alkyl radicals having from one to eleven carbon atoms, branched chain alkyl or cycloalkyl radicals having from three to twelve carbon atoms, or hydrocarbon radicals with from six to twelve carbon atoms comprising at least one aromatic ring, or where one or both of $R_5$ and $R_6$ are $COR_7$ and $R_7$ is hydrogen, a straight chain or branched chain alkyl radical with from one to twelve carbon atoms or a hydrocarbon radical with from six to twelve carbon atoms comprising at least one aromatic ring.

* * * * *

UNITED STATES PATENT AND TRADEMARK OFFICE
CERTIFICATE OF CORRECTION

PATENT NO. : 4,128,494
DATED : December 5, 1978
INVENTOR(S) : JEAN-PIERRE SCHIRMANN ET AL It is certified that error appears in the above-identified patent and that said Letters Patent are hereby corrected as shown below:

On title page of the patent following data element [22], insert
-- [30]  Foreign Application Priority Data
   September 1, 1976   France   76/26325 - -.

Column 3, line 6, after "1.7" insert --g--; line 24, before Table at line 25, insert --The following results are obtained: --.

Column 4, line 40, after "COR$_7$" insert --and R$_7$--.

Signed and Sealed this

Twentieth Day of March 1979

[SEAL]

Attest:

RUTH C. MASON
Attesting Officer

DONALD W. BANNER
Commissioner of Patents and Trademarks